(12) United States Patent
Yarovesky

(10) Patent No.: US 9,687,326 B2
(45) Date of Patent: *Jun. 27, 2017

(54) PROCESS FOR MAKING A DENTAL RESTORATION AND RESULTANT APPARATUS

(71) Applicant: Uriel Yarovesky, Thousand Oaks, CA (US)

(72) Inventor: Uriel Yarovesky, Thousand Oaks, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/611,481

(22) Filed: Feb. 2, 2015

(65) Prior Publication Data

US 2015/0150661 A1 Jun. 4, 2015

Related U.S. Application Data

(63) Continuation of application No. 12/115,967, filed on May 6, 2008, now Pat. No. 8,945,665.

(60) Provisional application No. 61/024,498, filed on Jan. 29, 2008.

(51) Int. Cl.
| | | |
|---|---|---|
| *A61C 13/08* | (2006.01) | |
| *A61C 5/10* | (2006.01) | |
| *A61C 13/00* | (2006.01) | |
| *A61C 13/09* | (2006.01) | |

(52) U.S. Cl.
CPC .............. *A61C 13/082* (2013.01); *A61C 5/10* (2013.01); *A61C 13/0004* (2013.01); *A61C 13/09* (2013.01)

(58) Field of Classification Search
None
See application file for complete search history.

(56) References Cited

U.S. PATENT DOCUMENTS

| | | |
|---|---|---|
| 4,207,678 A | 6/1980 | Jeannette |
| 4,657,399 A | 4/1987 | Hall |
| 4,802,850 A | 2/1989 | Boon |
| 4,828,117 A | 5/1989 | Panzera et al. |
| 5,004,417 A | 4/1991 | Giaramita |
| 5,114,340 A | 5/1992 | Hahn |
| 5,240,414 A | 8/1993 | Thompson |
| 5,529,492 A | 6/1996 | Yarovesky et al. |
| 2003/0224318 A1* | 12/2003 | Weinstein ............... A61C 19/10 433/26 |
| 2005/0074721 A1* | 4/2005 | Kim ................... A61C 13/0835 433/208 |

* cited by examiner

*Primary Examiner* — Christopher M Rodd
(74) *Attorney, Agent, or Firm* — Pasadena Legal Group; Norman R. Van Treeck

(57) ABSTRACT

A process for making a dental restoration includes forming a dental restoration base, selecting a decal representing a natural oral cavity characteristic, and attaching the selected decal to the base. Thereafter, the decal and the dental restoration base are conditioned to create a finished dental restoration having desired oral cavity color and characteristics such as teeth, enamel, dentin, crazing lines, stains, veins, blood vessels, bony coloration, hyper-calcification, mucosal tissue or gum tissue. In an alternative embodiment, the process may include placing a sealant over the decal and at least a portion of the dental restoration base. Additionally, a secondary decal may be attached over the sealant, followed by glazing the secondary decal.

2 Claims, 9 Drawing Sheets

PROCESS FOR MAKING A DENTAL RESTORATION AND RESULTANT APPARATUS

RELATED APPLICATION

This application is a continuation of U.S. application Ser. No. 12/115,967, filed May 6, 2008, now U.S. Pat. No. 8,945,665, issued Feb. 3, 2015.

BACKGROUND OF THE INVENTION

The present invention relates to a process for making a dental restoration and the resultant apparatus. More particularly, the present invention relates to a process for attaching a decal to a resultant dental appliance for creating a dental restoration having desired color and characteristics similar in appearance to natural teeth and/or oral tissue.

Dental restorations, in general, are fabricated to replicate the natural anatomical appearance in the oral cavity. This fabrication process is highly dependent on the artistic abilities of dental technicians. This dependence creates a difficulty among dental laboratory owners and dentists to produce consistent quality for patients. The reason for this difficulty lies in the fact that there are relatively few dental technicians that have the artistic ability or experience to artistically perform dental restorations to a level necessary to achieve high aesthetic results. This creates a high demand for experienced dental technicians and correspondingly drives up costs as there are few dental technicians with the requisite experience. Such high costs make it difficult for laboratories to stay competitive in a global market.

A current dental restoration trend is to use veneers, which are a thinner, more conservative tooth restoration. These restorations are applied with the dentist removing little or no natural tooth structure. The sacrifice for this type of restoration is that, while the natural tooth stays relatively intact, the thin structure of the veneer provides little to no room for the laboratories to create the natural aesthetics that are achieved using three dimensional color and structures. Many patients do not understand the anatomy of a tooth and do not understand the importance of these structures in making smiles appear natural. Most dentists understand the importance of preserving the natural tooth for the purpose of maintaining a sound structure. For this reason, some dentists may choose to make any necessary changes using minimally invasive dentistry. But, dentists are forced to use these thin veneers because of mass marketing to the public. Some dentists provide these restorations only to meet patient demand. The present invention endeavors to allow dentists to continue offering these conservative restorations without sacrificing the natural appearance of the restored tooth.

Thus, there is a need in the art for a process for making a dental restoration, and resultant apparatus, having desired color and characteristics similar to the natural oral cavity and applicable to crowns, bridges, ceramic restorations, resin, denture teeth, veneers, pre-fabricated matrixes, pre-cured resins and composites, and any other kind of restorative dental appliance.

SUMMARY OF THE INVENTION

The present invention is directed to a process for making a dental restoration and the resultant apparatus. The process for making the dental restoration includes the step of forming a dental restoration base. The dental restoration base preferably includes a dentin resin (e.g. for a chipped-tooth restoration), a veneer, or an acrylic or semi-transparent acrylic resin. Next, a decal which represents a natural oral cavity and color characteristic is selected. The natural oral cavity color and characteristic typically simulates teeth, tooth structure, dentinal variations, maverick colors, enamel, internal transparent areas of the tooth, crazing lines, stains, veins, blood vessels, bony coloration, hyper-calcification, mucosal tissue or gum tissue coloring. The selecting step also includes the steps of drawing or photographing an image of the tooth or tissue structure coloring characteristics, shrinking the image to the approximate size of the tooth and printing the image into a decal. The present invention may also include the step of creating a distributable picture, for use in the dental office, which matches the decal.

Next, the decal is attached to the dental restoration base. Thereafter, the decal and the base are conditioned in order to create a finished dental restoration having the desired color and characteristics. The conditioning step may include the step of curing the decal and the dental restoration base with a high intensity light. Alternatively, the conditioning step may include the step of firing the decal and the dental restoration base in an oven. The finished dental restoration may have a sealant placed over the decal and at least a portion of the dental restoration base for protection thereof. Preferably, the sealant comprises a composite resin, a semi-transparent acrylic resin, a protective layer, a ceramic or a glaze. Moreover, the present invention may include the alternative steps of glazing the decal, attaching a secondary decal over the sealant and subsequently glazing the secondary decal.

The resultant dental restoration apparatus includes a dental restoration base made from a composite resin, a veneer, ceramic or an acrylic resin. A decal is attached to the dental restoration base. The decal preferably has selected oral cavity color and characteristics of the natural oral cavity of the patient. Such color and characteristics should simulate teeth, crazing lines, enamel, dentin, stains, veins, blood vessels, bony coloration, hyper-calcification, mucosal tissue or gum tissue. A sealant may be disposed over the decal and at least a portion of the dental restoration base for protection thereof. The sealant preferably includes a composite resin, a semi-transparent acrylic resin, a protective layer, a ceramic or a glaze. Moreover, a secondary decal may be affixed to the sealant to provide additional coloring to the dental restoration.

Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
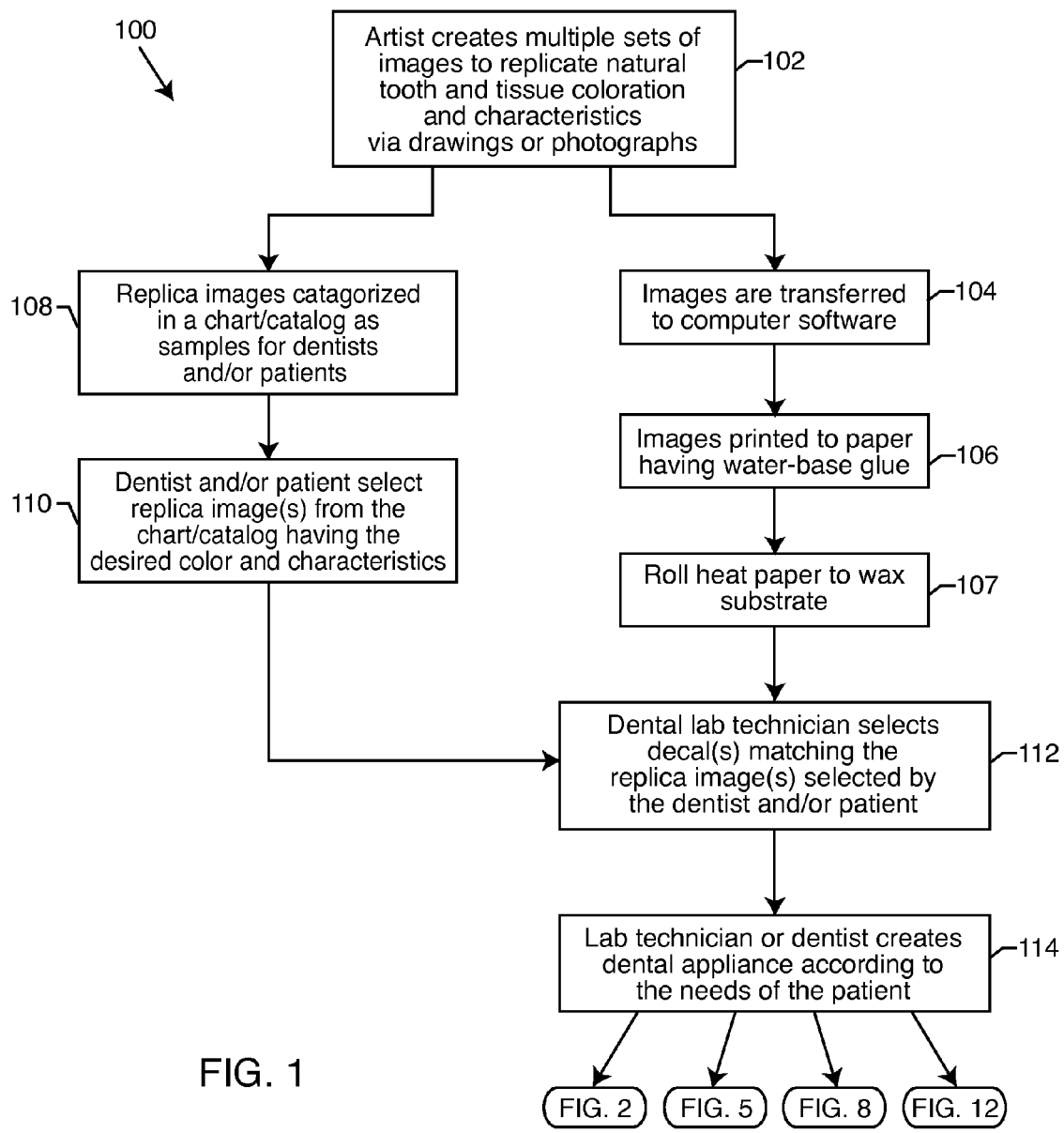
FIG. 1 is a flowchart illustrating the process of producing and selecting a decal for use in a dental appliance.

The present invention resides in a process for making a dental restoration having a decal therein, and the resultant apparatus. The decals are designed to replicate the natural anatomical appearance of the oral cavity. Specifically, the decals are designed to replicate tooth coloration, crazing lines, internal coloration, hyper-calcification, transparency, enamel variation, veins, white stains, lines in teeth, and other tissue and tooth colorations artistically difficult to replicate. FIG. 1 illustrates a flowchart for a process of creating decals for placement in dental appliances (100). First, an artist creates multiple sets of images to replicate natural tooth and tissue coloration and characteristics (102). The decal is made from artwork drawn out manually in a large format on an 8×10 sheet to provide accurate painted details of internal and external structures, characteristics and coloration of teeth and oral cavity tissue. The artist may choose to draw the decals based on photos or drawings of internal and external tooth and oral cavity tissue pictures. Alternatively, the decals may be printed directly from photographs of the teeth of the patient, or another person. The artist may manipulate the photographs with computer software to obtain the desired shape and color desired by the patient. Accordingly, the decals will vary in style, color, characteristics and may vary in size depending on the patient. The decals may include additional anatomical details such as mucosal tissue replication, veins, blood vessels, mimic bony coloring, hyper-calcification, crazing lines or any other natural or unnatural effects that affect tooth and oral cavity tissue color and characteristics. Appropriately, the decals will vary according to the application and desired use.

Once the details of the artwork are complete, the artwork is reduced in size to the size of natural teeth for dental application. The smaller size images are then transferred to computer software (104) suitable for printing the images to paper (106). Next, the paper, having a water-based glue thereon, is roll heated to a wax substrate (107). The decal remains on the wax substrate as the paper and wax substrate are separated. The decal on the wax substrate may also include a color pigment, such as an opaque level, that facilitates blocking unwanted discoloration in cases where severe discoloration exists. Alternatively, the decals can be used to block out the darker background portion of a tooth to achieve lighter and brighter results. Alternatively, the decal may introduce desired color and structures within this layer. Accordingly, the printed decals are capable of being hardened to a composite resin, an acrylic resin or ceramic for secure attachment within the dental restoration. The versatility of such decals is virtually unlimited and can be used to recreate any type of dental effect, both existing structures and non-existing structures in the oral cavity.

Next, replica images are categorized in a chart and/or catalog as samples for viewing by dentists and/or patients (108). The catalog will include a variety of styles, colors and stylizations for the dentist to share with the patient in preparation for creating a dental restoration. The catalog is representative of the types of decals that are available at the dental laboratory, or any other facility where dental restorations are fabricated. Accordingly, the dentist and patient select a replica image or multiple replica images from the chart/catalog having the desired color and characteristics for the tooth or tissue restoration (110). The selected decal should have the appropriate color and transparency characteristics that match the natural oral cavity coloration and characteristics the patient desires. The dentist then communicates the selected decals to the dental lab technician at a facility that manufacturers the tooth restoration. From this information, the dental lab technician selects a decal, or multiple decals, matching the replica image, or multiple replica images, selected by the dentist and patient (112). The lab technician chooses the corresponding decals from the artist decal sheet to match the chosen images selected by the dentist and/or patient (110). The lab technician or dentist then creates the dental appliance according to the needs of the patient (114), as specifically described in the flowcharts in FIGS. 2, 5, 8 and 12.

The reference catalog provided to dentists helps ensure the consistency and accuracy of selecting a particular style decal needed for the tooth restoration. Manufacturers and laboratories will have corresponding transparent decals that match the replica images selected by the dentist and/or patient. The decals are applied to the selected dental appliance. This method increases the aesthetic predictability of the appearance of the tooth restoration and virtually eliminates the difficult task of artistically mimicking the natural color and characterization of the oral cavity, one patient at a time. The present invention also reduces the need for training technicians to fabricate artistically realistic tooth restorations and transforms the manufacturing process into a much simpler technique, especially for ceramic teeth manufacturing used with dentures. As a result, the present invention will allow manufacturers to reduce the cost of tooling as multiple layer manufacturing of denture teeth will no longer be needed.

Figure 2:
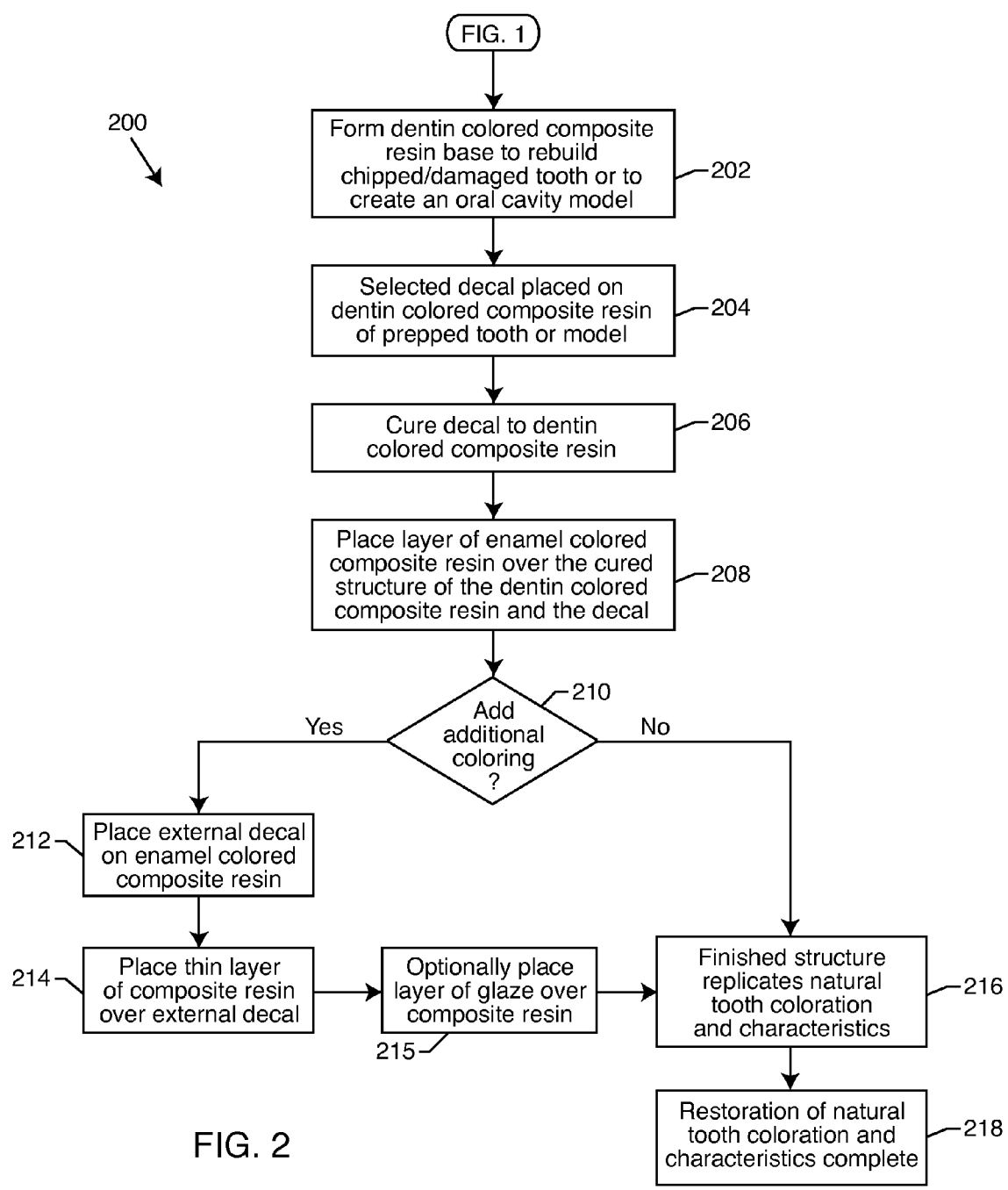
FIG. 2 is a flowchart illustrating the process of incorporating a decal in a composite resin-based dental restoration.

FIG. 2 illustrates a process for creating an oral cavity model or restoring a natural tooth, due to breakage, chipping or grinding (200). The first step is to apply a dentin colored composite resin to rebuild the chipped and/or damaged tooth (202). The dentin colored composite resin also forms the base of the oral cavity model. The dentin colored composite resin varies in coloration, but is commonly some shade yellow. For a damaged natural tooth, the dentin colored composite resin is placed in an appropriate location to create a fairly flat platform to allow the decals to conform to the surface thereof. Hardening the dentin colored composite resin is accomplished by any one of several polymerization processes. In one embodiment, the dentin colored composite resin is hardened using a halogen-based bulb that concentrates a specific wavelength of light on the composite resin. A chemical catalyst in the composite resin is sensitive to the light. When exposed to the light, the composite resin hardens. A light-based hardening process may be accomplished chair side. Alternatively, non-chair side processes may include using pressure or heat to further harden the dentin colored composite resin. These hardening procedures are typically used to create model teeth or for replacement teeth for use in dentures or partials. In one embodiment, pressure is used to remove air gaps within the composite resin material to increase the density thereof thereby forming a harder structure than if only hardened by light. Accordingly, light may be used to further harden the structure by reacting with a chemical catalyst in the composite. In another alternative embodiment, the light and pressure is combined with heat. In this embodiment, the dentin colored composite resin achieves a high degree of polymerization at high intensity temperatures as high as 1700° F. Chemical catalysts in the composite resin react and harden at these high temperatures. Alternatively, the heating and pressurizing processes may be used exclusively without light. Different chemical compounds may be used in the composite resin depending on the desired polymerization process. Accordingly, the dentist or dental technician would endeavor to select the corresponding chemical catalyst that hardens in response to light, pressure or heat.

Next, the selected decal is placed on the hardened dentin colored composite resin of the model or prepped tooth (204). The decal is then cured to the dentin colored composite resin (206). To complete the initial contour and shape of the restored tooth, a layer of enamel colored composite resin is placed over the cured structure of the dentin colored composite resin and the decal (208). The dentist must then decide whether to add additional coloring (210). When adding additional coloring, an external decal is placed over the layer of enamel colored composite resin (212) to add the necessary stylizations to replicate the natural tooth colorizations and characteristics. Next, a thin layer of composite resin is placed over the external decal (214). Thereafter, an optional layer of glaze is placed over the composite resin (215) to protect the dental restoration from possible long-term deterioration. Decals can be used on external surfaces to achieve the desired colorization results. This application may also be used for pressable or milled ceramics for any ceramic restoration (tooth and oral tissue, such as mucosal tissue) that requires limited coloration variations where additional stylizations will enhance the overall aesthetic results of the tooth restoration, as further described herein. The completed structure should replicate the natural tooth coloration and characteristics (216) such that the restoration of the natural tooth coloration and characteristics is complete (218).

Figure 3:
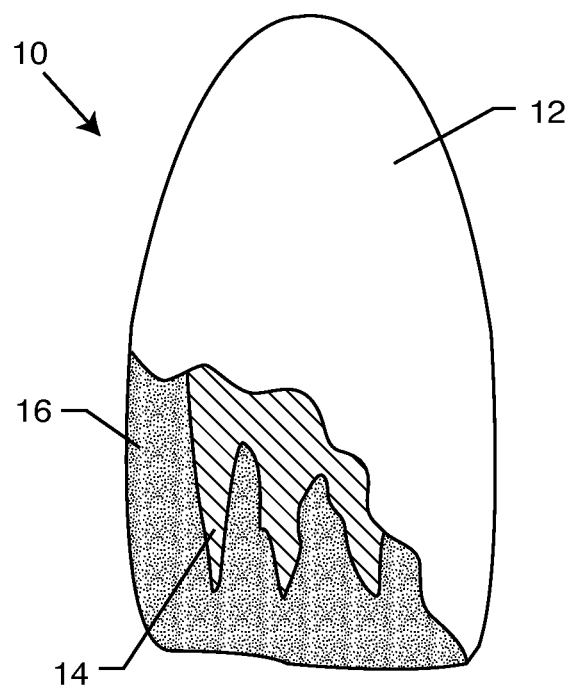
FIG. 3 is a front view of a rebuilt chipped tooth having a decal therein.
Figure 4:
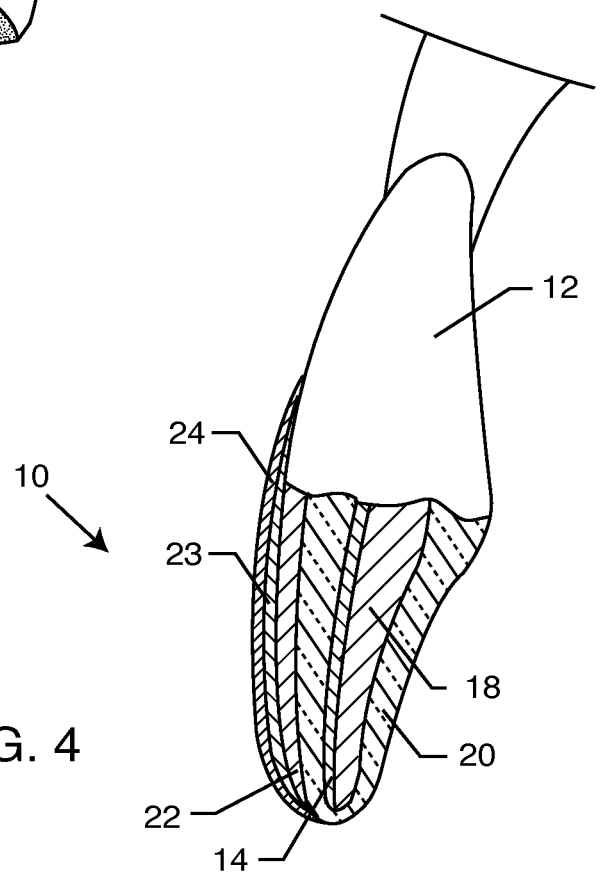
FIG. 4 is cross-sectional view of a restored chipped tooth, including an external decal having a glaze thereover.

FIGS. 3 and 4 illustrate a tooth restoration 10 of a chipped tooth 12 having a decal 14 therein. FIG. 3 is front view of the tooth restoration 10 wherein a portion of the chipped tooth 12 is filled in with a filler 16. As shown in FIG. 4, the filler 16 comprises a dentin colored composite resin base 18 having the decal 14 formed thereon. Accordingly, after the decal is cured as described in step (206), an enamel colored composite resin 20 is disposed over the decal 14 and the dentin colored composite resin base 18. This filler 16 is designed to fix a cracked or broken portion of the tooth 12, generally shown in FIG. 3. The decal 14 is displayed through the enamel colored composite resin 20 such that the colorization and characteristics of the decal 14 are viewable as shown through the front side of the chipped tooth 12 in FIG. 3. An additional external decal 22 may be disposed on top of the enamel colored composite resin 20 for additional coloring or characteristics. The external decal 22 may be protected by a applying a thin layer of composite resin 23 thereover. Optionally, a substantially transparent glaze surface 24 may be applied to the thin layer of composite resin 23 for further protection thereof.

In an alternative embodiment, the tooth restoration 10 of FIGS. 3 and 4 could be used to create an oral cavity model. The process for making the model is generally illustrated in the flowchart in FIG. 2. The model comprises similar compositions as the tooth restoration illustrated in FIG. 4. Of course, the model would not include a portion of a natural chipped tooth 12. Therefore, the dentin colored composite resin base 18, the enamel colored composite resin 20, the decal 14 and the thin composite resin layer 23 would extend the entire length of the tooth restoration 10 as shown in partial form in FIG. 4. Likewise, the external decal 22 and optional glaze surface 24 should also extend the length of the model. The decal 14 or the external decal 22 may be applied as a whole sheet or as a series of partial sheets in sections of the front, back and bottom portions of the tooth. This process further ensures accurate replication of natural tooth colorization and characteristics.

Figure 5:
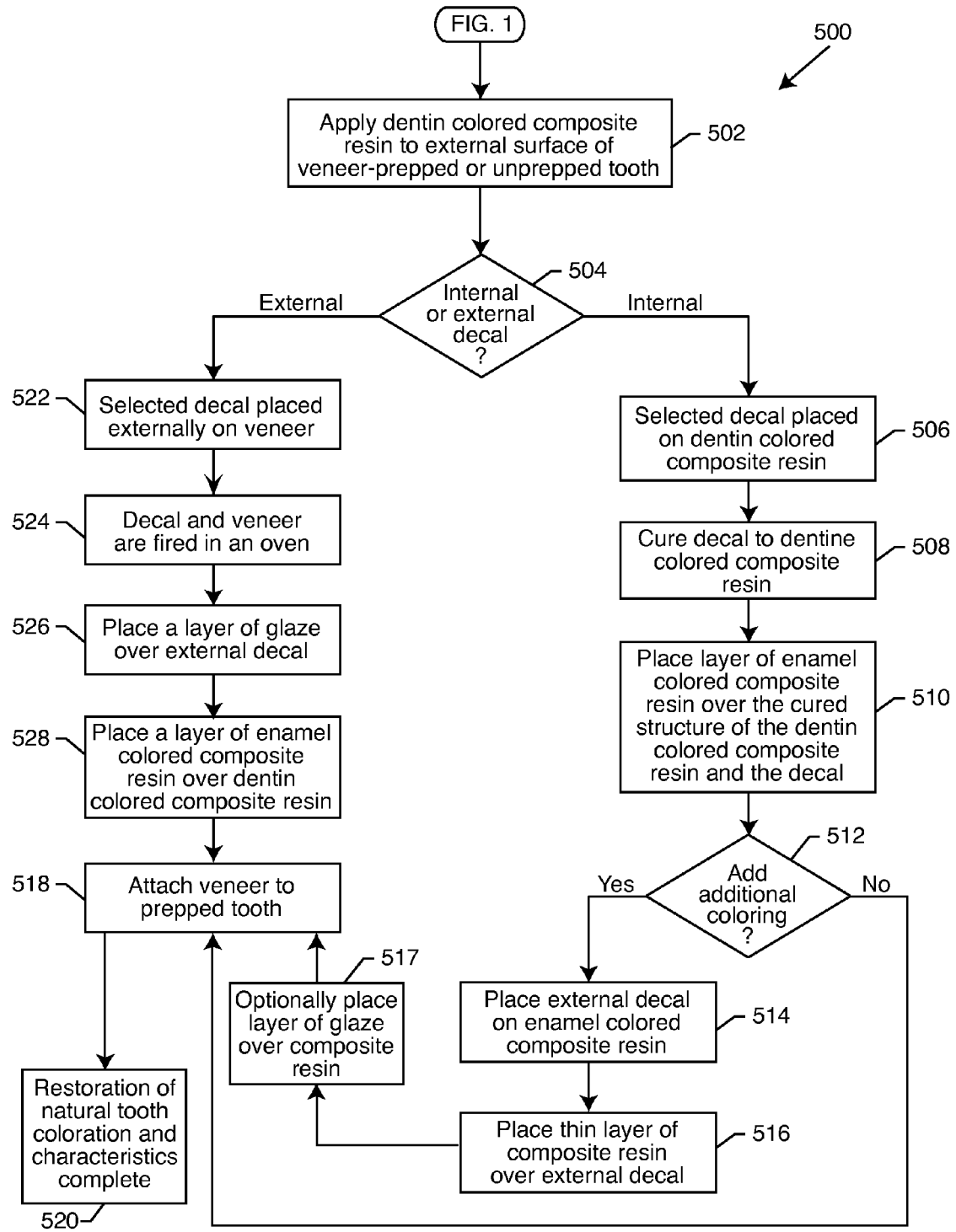
FIG. 5 is a flowchart illustrating the process of incorporating a decal into a veneer-based dental restoration.

Alternatively, the present invention may also be applied to composite resin-based or porcelain-based veneers. FIG. 5 illustrates a process for creating a tooth restoration using a decal and a composite resin-based veneer (500). The first step is to apply the dentin colored composite resin to an external surface of the veneer-prepped tooth (502). Accordingly, step (502) involves shaving a portion of the existing tooth enamel down to make room for the necessary depth of the veneer. Prepping a tooth for veneer placement is well-known in the art. Alternatively, the dentin colored composite resin may be applied to an unprepped tooth. In this embodiment, a portion of the existing tooth enamel does not need to be shaved prior to the subsequent steps described below.

The next step is to determine whether the decal will be placed internal or external in the tooth restoration (504). Internal placement of the decal on the tooth restoration is similar to the process disclosed in FIG. 2. First, the selected decal is placed on the dentin colored composite resin of the prepared tooth (506). Next, the decal is cured to the dentin colored composite resin (508) by any of the previously described methods. Then, a layer of enamel colored composite resin is placed over the dentin colored composite resin and decal (510). Sometimes only a small layer of dentin colored composite resin is required because the tooth may not be chipped as previously described and shown in FIGS. 3 and 4. Similar to FIG. 2, the dentist must next determine whether to add additional coloring (512) to the tooth restoration. In the case that additional coloring is desired, an external decal is placed on the enamel colored composite resin (514) followed by placing a thin layer of composite resin over the external decal (516). Optionally, a layer of glaze may be placed over the composite resin (517) for further protection of the dental restoration. The external decal is placed over the enamel colored composite resin to further enhance the natural aesthetic look of the restored tooth. Thereafter, the prepped tooth is ready to have the veneer attached thereto (518). The restoration of the natural tooth coloration and characteristics is then complete (520) for that tooth. The steps for creating a tooth restoration with a decal and a composite resin-based veneer (500) and specifically steps (502)-(517), may be repeated for multiple teeth. Often it is desirable to restore more than one tooth with veneers to ensure color consistency and characteristics among the restored teeth and non-restored teeth.

Alternatively, the process for creating a tooth restoration with a decal and a composite resin-based veneer (500) may include the step of placing the decal external to the tooth restoration. As shown in FIG. 5, after deciding to use an external decal (504), the selected decal is externally placed on the veneer (522) before attachment to a natural tooth. Next, the veneer and decal are fired in an oven (524). Thereafter, a layer of glaze (526) is placed over the external decal for protection thereof. A layer of enamel colored composite resin is placed over the veneer-prepped tooth (528) such that the veneer may be attached to the tooth (518), as previously described. Accordingly, the veneer is then attached to the prepped tooth (518). The restoration of the natural tooth coloration and characteristics is then complete (520). Similarly, steps (502)-(526) may be repeated for each veneer the patient requires.

Figure 6:
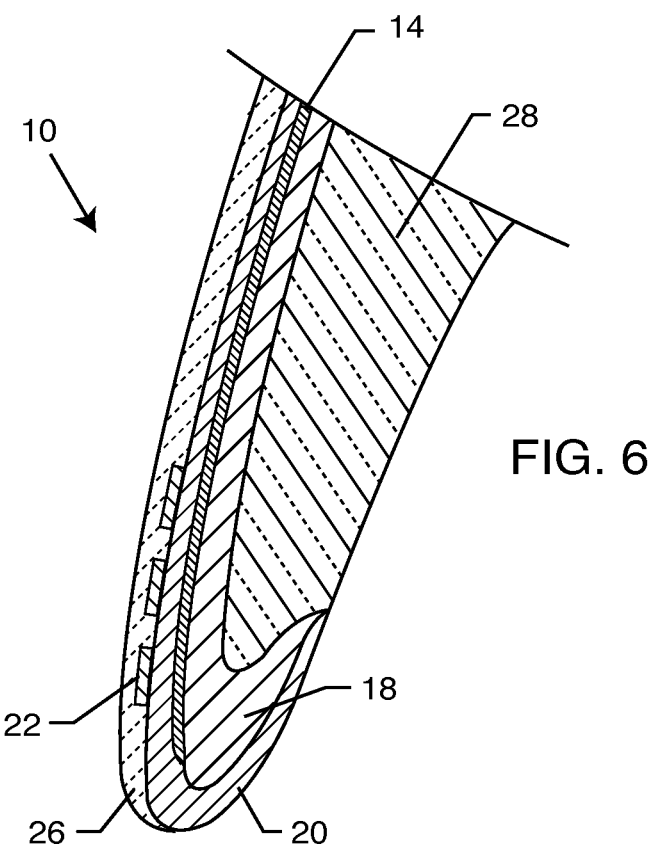
FIG. 6 is a cross-sectional view of an internal decal incorporated into a veneer-based dental restoration.
Figure 7:
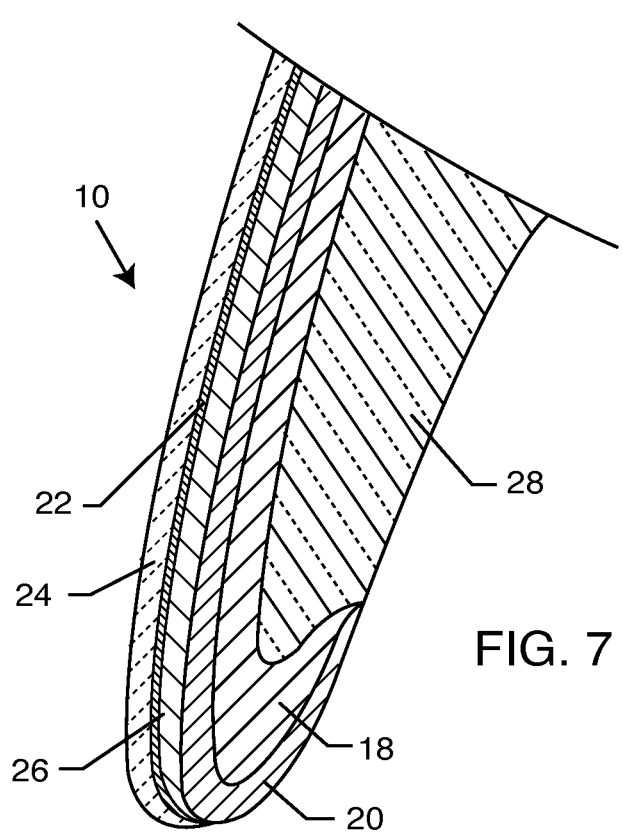
FIG. 7 is a cross-sectional view of an external decal overlying a veneer.

FIGS. 6 and 7 are cross-sectional side views of a tooth restoration 10 finalized with a composite resin-based veneer 26. FIG. 6 illustrates the tooth restoration 10 having an internally placed decal 14. As shown, a veneer prepped tooth 28 has a dentin color composite resin base 18 applied along the exterior thereof. The veneer-prepped tooth 28 may be reduced slightly in size (e.g. 1.5 millimeters) to make room for the veneer 26 and the corresponding dentin colored composite resin base 18, enamel colored composite resin 20 and the decal 14. Accordingly, the decal 14 is applied to the external front layer of the dentin colored composite resin base 18. The enamel colored composite resin 20 is thereafter applied to the external surface of the decal 14 and the dentin colored composite resin base 18. An alternative external decal 22 may be applied to the enamel colored composite resin 20 before application of the veneer 26. Once the dentist determines that the appropriate colorization and characterization of the tooth are adequate, the veneer 26 is attached thereto according to the processes described above.

FIG. 7 illustrates attachment of the composite resin-based veneer 26 to the veneer-prepped tooth 28 utilizing only the external decal 22. As shown in FIG. 7, the veneer-prepped tooth 28 has the dentin colored composite resin base 18 applied thereto. The enamel colored composite resin 20 is applied directly to the dentin colored composite resin base 18. The veneer 26 having the external decal 22 and the glazed surface 24 thereover is thereafter attached to the enamel colored composite resin 20 by any method known in the art. The attached veneer 26 then displays the desired coloration and characteristics of the natural tooth via the external decal 22.

Figure 8:
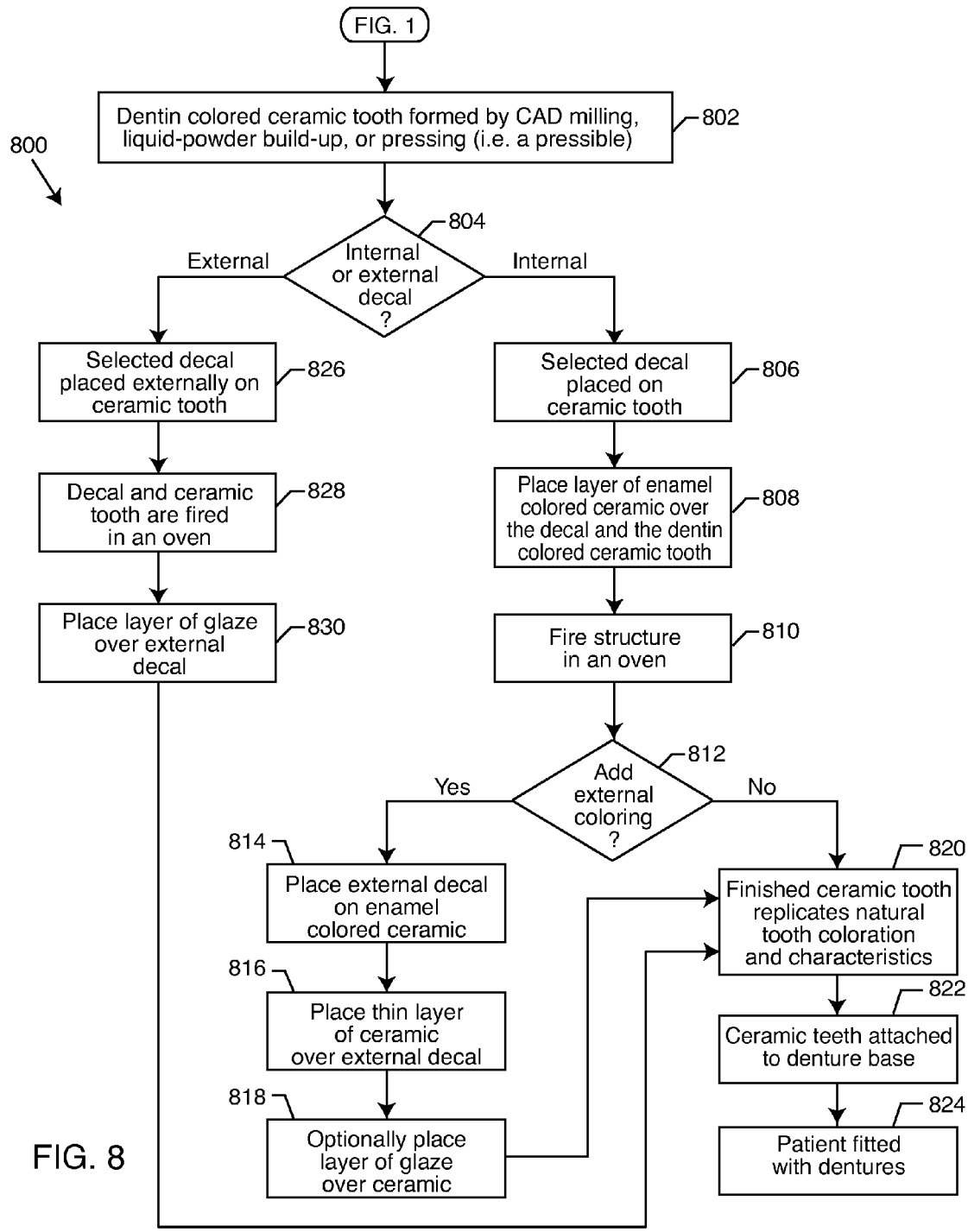
FIG. 8 is a flowchart illustrating a process of incorporating a decal into ceramic tooth.

The present invention may be used with a dentin colored ceramic tooth for placement in dentures, as generally shown in the flowchart in FIG. 8. In most instances, the steps in FIG. 8 may be accomplished by a ceramic tooth manufacturer, rather than a dentist or lab technician. Multiple decals may be needed in order to replicate the coloration and characteristics of multiple teeth that the dentures will replace. The use of decals in the fabrication phase of ceramic teeth for use in dentures simplifies the production process and provides more realistic dentures. The fabricated ceramic teeth contain better aesthetic coloration and characteristics.

The process for forming a ceramic tooth for placement in dentures (800) starts by forming a dentin colored ceramic tooth via CAD/CAM milling, liquid-powder build-up, or pressing (i.e. a pressible) (802). The next step is to determine whether the decal will be placed internal or external in the dentin colored ceramic tooth (804). Internal placement of the decal on the dentin colored ceramic tooth is similar to the process disclosed in FIG. 5. First, the selected decal is placed on the dentin colored ceramic tooth (806). Next, a layer of enamel colored ceramic is placed over the decal and the dentin colored ceramic tooth (808). The structure that includes the dentin colored ceramic tooth, the decal and the enamel colored ceramic is then fired in an oven for hardening (810). Thereafter, the ceramic tooth manufacturer or subsequent dental lab technician may determine whether or not to add external coloring (812). In the event that the external coloring is desired, an external decal is placed on the enamel colored ceramic (814). A thin layer of ceramic is then placed over the external decal (816). Optionally, a layer of glaze is then placed over the ceramic (818) for further protection thereof. The finished ceramic tooth should accurately replicate natural tooth coloration and characteristics (820). The necessary quantity of ceramic teeth is then attached to the denture base (822). Thereafter, the patient is fitted with the dentures (824) having a natural look. Alternatively, it may be decided that external coloring is not needed (812), wherein the dentures are finished (820) without any additional steps. Accordingly, the ceramic teeth are attached to the denture base (822) and then fitted to the patient (824).

Alternatively, it may be determined during step (804) that the decal is to be placed external in the tooth restoration. In this embodiment, the selected decal is placed externally on the ceramic tooth (826). Next, the decal and ceramic tooth are fired in an oven (828). This hardens the resultant structure. A layer of glaze is then placed over the external decal (830). The finished ceramic tooth replicates the natural tooth coloration and characteristics of the oral cavity (820). The requisite quantity of ceramic teeth are then attached to the denture base (822) before the patient is fitted with the dentures (824).

The process illustrated in FIG. 8 is tremendously advantageous over current practices in that the ceramic teeth of the dentures include actual color and characteristics without spending hours in an artistic studio drawing the details. Ceramic teeth otherwise not having these details appear unnaturally consistently white (or a shade thereof). This is an undesirably unnatural look. The present invention eliminates the time and cost associated with an artist adding the necessary details to make the teeth look natural.

Figure 9:
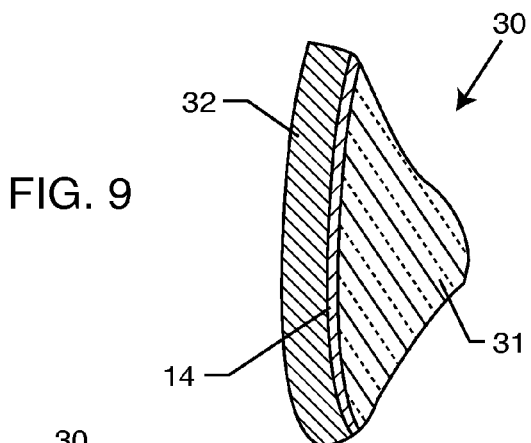
FIG. 9 is a cross-sectional view of a decal located between an enamel colored ceramic and a dentin colored ceramic in the ceramic tooth.
Figure 10:
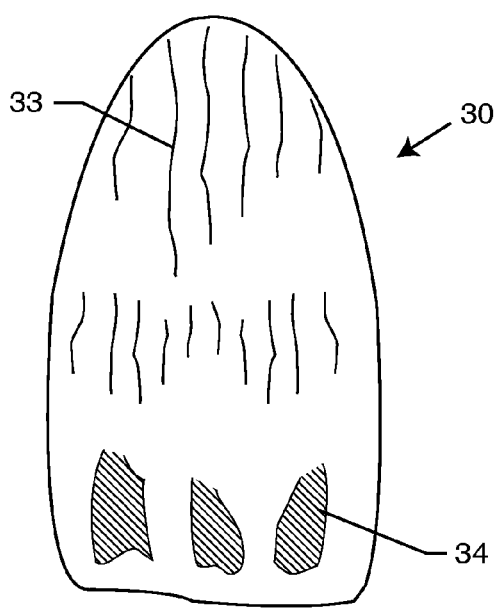
FIG. 10 is a front view of a ceramic tooth having a decal located therein, illustrating detail lines and coloration.
Figure 11:
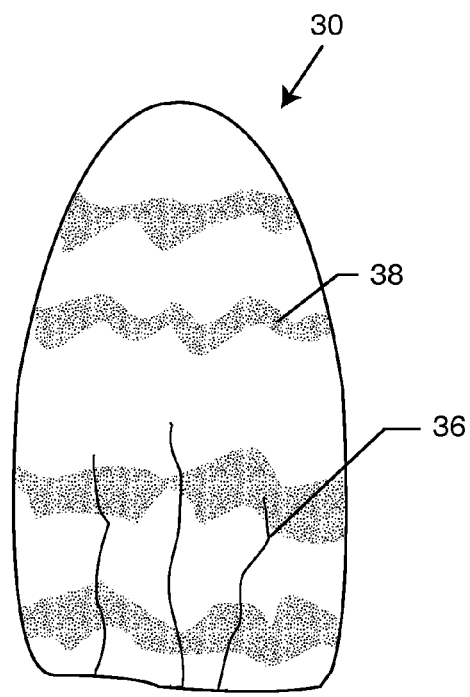
FIG. 11 is a front view of a ceramic tooth having a decal located therein, illustrating crazing lines and other characterizations.

FIGS. 9-11 illustrate a sample ceramic tooth 30 for placement in dentures. FIG. 9 illustrates a cross-sectional view of the ceramic tooth 30 comprising a dentin colored ceramic base 31 having the decal 14 placed thereover and protected by an enamel colored ceramic 32. The stylizations of the internal decal 14 placed between the dentin colored ceramic base 31 and the enamel colored ceramic 32 are visible through the enamel colored ceramic 32. FIG. 10 illustrates a front view of the ceramic tooth 30 having a plurality of details therein. For example, the ceramic tooth 30 includes a set of detail lines 33 and colorations 34. As more specifically shown in FIG. 11, the detail lines 33 may include a set of crazing lines 36 or white stains 38. In each of the embodiments illustrated in FIGS. 9-11, the ceramic tooth 30 has the decal 14 placed internally. The details illustrated in FIGS. 10 and 11 may come in many different types of stylizations, as previously described and listed. Moreover, the decal 14 may be placed externally (not shown). The decal may also be used in dentures with composite resin-based teeth in addition to the ceramic-based teeth.

Figure 12:
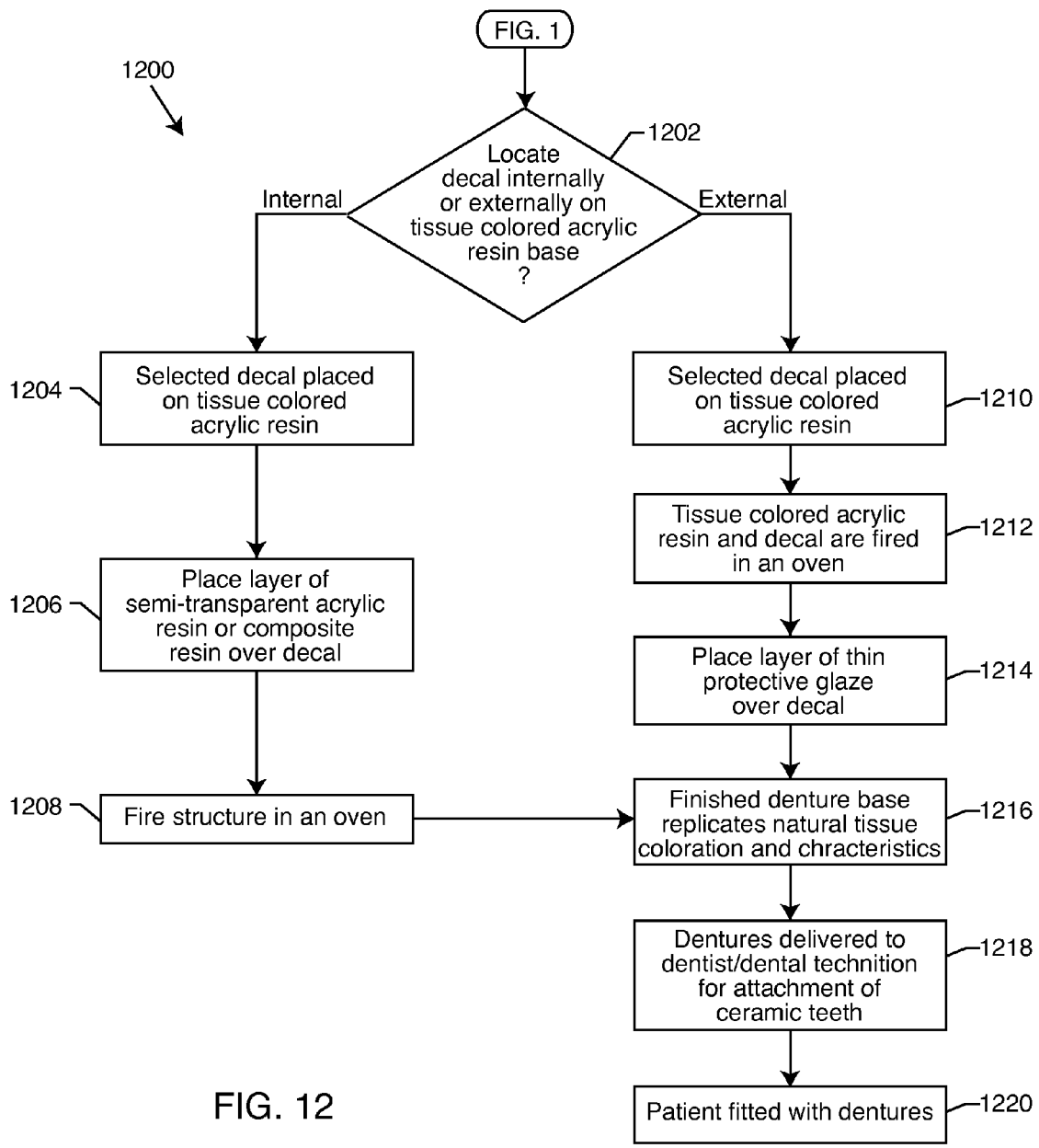
FIG. 12 is a flowchart illustrating the process of incorporating a decal into an acrylic resin representing tissue in dentures.

FIG. 12 illustrates the general process for incorporating a decal of the present invention in a dental appliance for replicating the natural color and characteristics of oral tissue (1200). First, a lab technician must determine whether the decal is to be located internally or externally on a tissue colored acrylic resin base (1202). An internally located decal is placed directly on the tissue colored acrylic resin (1204) in the dental appliance. These decals may, alternatively, be used to represent soft tissue coloration and characteristics and can be used in conjunction with veneers, crowns, bridges and other implants. The decals mimic the tissue stylizations applied to dental restorations when soft tissue prosthesis is necessary. A layer of semi-transparent acrylic resin or composite resin is then placed over the decal (1206). The tissue colored acrylic resin base and the decals are then fired in an oven (1208). External placement of the decal requires that the selected decal be placed on the tissue colored acrylic resin base (1210). This structure is then also hardened by firing in an oven (1212). Next, a thin layer of protective glaze is placed over the external decal (1214). The protective glaze provides insulation of the decal from the environment and protects against wear. The result of steps (1208) and (1214) is that the finished dental appliance replicates the natural tissue coloration and characteristics of the oral cavity (1216). The finished structure is then delivered to the dentist or a dental technician, for attachment of ceramic teeth (1218) before being fitted to the patient (1220). In this embodiment, the internal or external decals mimic the oral tissue coloring, which may comprise blood vessels, tissue covering, musculature areas, tendons, tissue colors or bony anatomy changes. The steps disclosed in FIG. 12 may also be combined with those steps disclosed in FIG. 8 to provide dentures having both natural looking teeth (FIGS. 9-11) and oral tissue (FIGS. 13-14).

Figure 13:
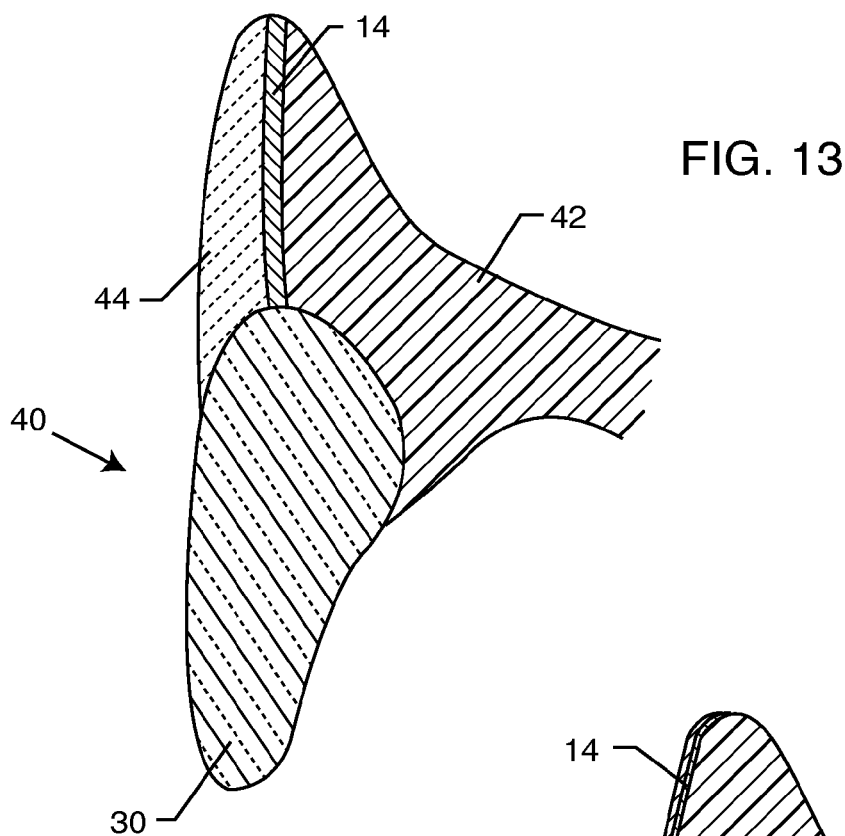
FIG. 13 is a cross-sectional view of an internally placed decal representing the tissue area of dentures.
Figure 14:
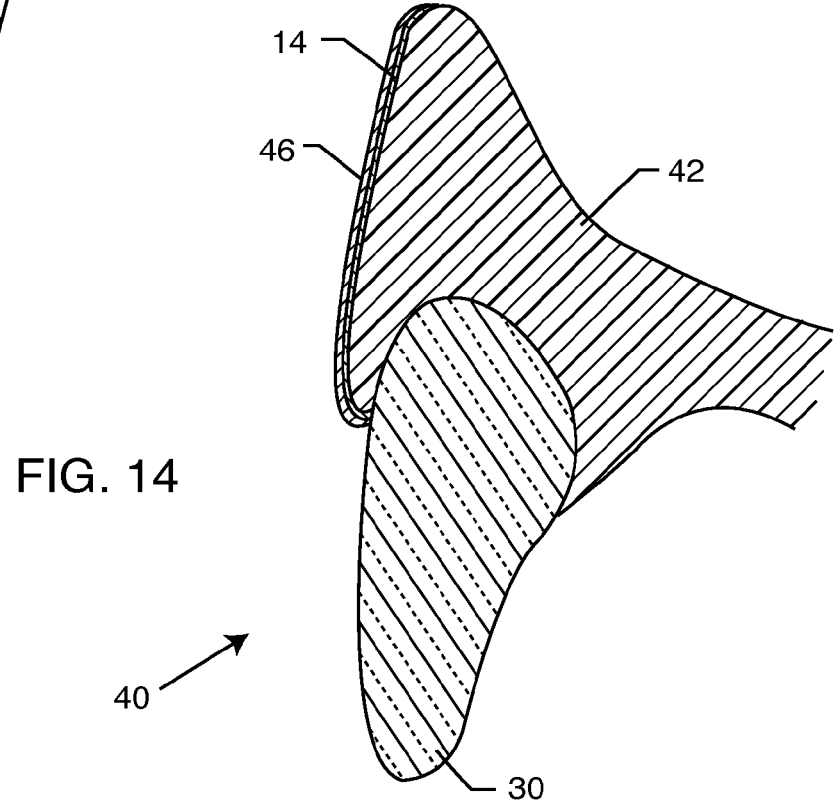
FIG. 14 is a cross-sectional view of an externally placed decal representing the tissue area of dentures.

FIGS. 13 and 14 illustrate the internal and external placement, respectively, of the decal in the oral tissue area of dentures. FIGS. 13 and 14 are a cross-sectional view of a denture 40, generally. Accordingly, the dentures 40 include a tissue colored acrylic resin 42 adjacent to the previously described ceramic tooth 30. In FIG. 13, the decal 14 is placed internal in the denture 40 as sandwiched between the tissue colored acrylic resin 42 and a semi-transparent tissue colored acrylic resin 44. The semi-transparent tissue colored acrylic resin 44 allows the details of the decal 14 to be seen externally. Thus, the natural tissue coloration the decal 14 aims to display is visible. Alternatively, in FIG. 14 the decal 14 is external to the tissue colored acrylic resin 42 and is protected by a protective layer 46. Preferably the protective layer 46 is the previously described glaze.

In general, the decals of the present invention are fabricated from a photo, captured image or drawing to aesthetically mimic the internal and/or external coloration and characteristics of natural teeth and the internal and/or external coloration and characteristics of natural tissue surrounding tooth areas, such as papillae and mucosal tissue. The fabrication of the composite resin restorations, either directly or indirectly, includes placing a decal or part of a decal in a composite resin or ceramic fabrication to mimic the internal and external anatomical coloration of the oral cavity. Mimicking the natural color stylizations allows dentists to offer patients dental restorations having tooth and tissue coloration and characteristics, within a thin dimension, that best matches the oral cavity aesthetics of the patient.

The decals can create a three-dimensional natural looking tooth restoration by placing the decals in multiple layers of composite resin or ceramic material. Alternatively, the multiple decals may be stacked on one another or placed intermittently in the front, bottom or rear portions of the tooth restoration. The key aspect of the present invention is that the decal replaces any need for drawing tooth or tissue coloration and characteristics to the dental restoration. The composite resin, ceramic or glaze protect the decal to increase durability. The decals described herein can be placed in areas where composite resin layering, ceramic layering and acrylic resin layering are being used. Such layering may be used in the fabrication of denture teeth, tooth restorations or mucosal tissue replication. The present invention may also be used with partial veneers, crown and bridge applications and chipped or broken teeth as well as non-prepared teeth for veneering purposes.

Although several embodiments have been described in some detail for purposes of illustration, various modifications may be made to each without departing from the scope and spirit of the invention. Accordingly, the invention is not to be limited, except as by the appended claims.

What is claimed is:

1. A dental restoration, comprising:
   a dental restoration base comprising a composite resin, a ceramic or an acrylic resin, and attachable to a tooth of a patient or insertable in a mouth of a patient;
   a decal attached to the dental restoration base and having printed thereon an image of a selected natural oral cavity characteristic of the patient including tooth structure, enamel, dentin, crazing lines, stains, veins, blood vessels, bony coloration, hyper-calcification, mucosal tissue or gum tissue so as to mimic at least a portion of a natural tooth or oral cavity tissue, wherein the decal is printed from an image selected from a plurality of pre-made images similar in appearance to natural teeth or oral cavity tissue, wherein the image comprises a photograph, a computer-generated model image, or a drawing;
   a sealant disposed over the decal and at least a portion of the dental restoration base, wherein the sealant comprises a composite resin, a semi-transparent acrylic resin, a protective layer, or a glaze;
   a secondary decal affixed to the sealant to provide additional coloring to the dental restoration base; and
   a secondary sealant disposed over the secondary decal.

2. The dental restoration of claim 1, wherein one or more of the decal and the secondary decal is created from a distributable image.

* * * * *